(12) United States Patent
Burroughs et al.

(10) Patent No.: US 7,543,478 B2
(45) Date of Patent: Jun. 9, 2009

(54) DEVICE AND METHOD FOR DETECTING HAZARDOUS MATERIAL IN MAIL

(75) Inventors: Eric Gregory Burroughs, Reisterstown, MD (US); Kenneth Scott Damer, Parkville, MD (US); Matt Szarek, Dundalk, MD (US)

(73) Assignee: Northrop Grumman Systems Corporation, Los Angeles, CA (US)

( * ) Notice: Subject to any disclaimer, the term of this patent is extended or adjusted under 35 U.S.C. 154(b) by 106 days.

(21) Appl. No.: 11/783,811

(22) Filed: Apr. 12, 2007

(65) Prior Publication Data

US 2008/0250845 A1 Oct. 16, 2008

(51) Int. Cl.
*G01N 1/22* (2006.01)

(52) U.S. Cl. ............... 73/28.01; 73/31.01; 73/31.02; 73/31.03; 73/864.33

(58) Field of Classification Search .............. 73/23.2, 73/28.01, 31.01–31.04, 31.07, 863.21–863.23, 73/863.71, 864.33; 209/606, 655, 659, 663; 340/540, 632; 435/287.1, 587.1
See application file for complete search history.

(56) References Cited

U.S. PATENT DOCUMENTS

| | | | | |
|---|---|---|---|---|
| 4,987,767 A * | 1/1991 | Corrigan et al. | ............ | 73/23.36 |
| 5,465,828 A * | 11/1995 | Thomas et al. | ............ | 198/495 |
| 5,915,268 A * | 6/1999 | Linker et al. | ............ | 73/23.2 |
| 5,942,699 A * | 8/1999 | Ornath et al. | ............ | 73/863.21 |
| 6,085,601 A * | 7/2000 | Linker et al. | ............ | 73/863.12 |
| 6,324,927 B1 * | 12/2001 | Ornath et al. | ............ | 73/864.33 |
| 6,567,008 B1 * | 5/2003 | Sansone | ............ | 340/666 |
| 6,573,836 B1 * | 6/2003 | Gitis et al. | ............ | 340/603 |
| 6,613,571 B2 * | 9/2003 | Cordery et al. | ............ | 436/48 |
| 6,765,490 B2 * | 7/2004 | Lopez et al. | ............ | 340/632 |
| 6,792,795 B2 * | 9/2004 | Jones et al. | ............ | 73/37 |
| 6,811,587 B1 * | 11/2004 | Lorey et al. | ............ | 55/385.2 |
| 6,823,714 B2 * | 11/2004 | Megerle | ............ | 73/23.2 |
| 6,834,533 B2 * | 12/2004 | Megerle | ............ | 73/45.4 |
| 6,886,419 B2 * | 5/2005 | Cordery et al. | ............ | 73/863.23 |
| 6,888,085 B2 * | 5/2005 | Spencer et al. | ............ | 209/584 |
| 6,941,794 B2 | 9/2005 | Strohmeyer | | |
| 7,024,019 B2 * | 4/2006 | Sansone | ............ | 382/101 |
| 7,073,371 B2 * | 7/2006 | Strohmeyer et al. | ............ | 73/28.01 |
| 7,110,422 B1 | 9/2006 | Choudhury | | |
| 7,114,369 B2 | 10/2006 | Strohmeyer | | |
| 7,194,924 B2 * | 3/2007 | Wisniewski et al. | ............ | 73/863.21 |
| 7,232,070 B2 * | 6/2007 | Craig | ............ | 235/462.01 |
| 2002/0124664 A1 * | 9/2002 | Call et al. | ............ | 73/863.22 |
| 2003/0106362 A1 * | 6/2003 | Megerle et al. | ............ | 73/23.2 |
| 2003/0113922 A1 * | 6/2003 | Cordery et al. | ............ | 436/1 |
| 2003/0114957 A1 * | 6/2003 | Cordery et al. | ............ | 700/228 |
| 2003/0115161 A1 * | 6/2003 | Cordery et al. | ............ | 705/402 |
| 2003/0115998 A1 * | 6/2003 | Belec et al. | ............ | 83/343 |
| 2003/0119175 A1 * | 6/2003 | Stradley et al. | ............ | 435/287.1 |
| 2003/0136203 A1 * | 7/2003 | Yoon | ............ | 73/864.33 |

(Continued)

*Primary Examiner*—David A. Rogers
(74) *Attorney, Agent, or Firm*—Andrews Kurth LLP

(57) ABSTRACT

A mail screening device for hazardous materials is disclosed. The mail screening device comprises a sample collection unit that uses air jets or air knives to dislodge residues of hazardous materials from a mail, and a detection unit that detects the hazardous materials in the exhaust air flow. Comparing to traditional mail screening systems that use belts and rollers to physically pinch a mail for sample collection, the device of the present invention is less complex and easier to operate, thereby reducing installation, maintenance and replacement costs.

20 Claims, 10 Drawing Sheets

U.S. PATENT DOCUMENTS

| | | |
|---|---|---|
| 2003/0145664 A1* | 8/2003 | Schwarz et al. ......... 73/863.22 |
| 2004/0024278 A1* | 2/2004 | Megerle .................... 588/200 |
| 2004/0028561 A1* | 2/2004 | Daugherty et al. ............ 422/99 |
| 2004/0063198 A1* | 4/2004 | Tilles et al. .............. 435/287.2 |
| 2004/0076544 A1* | 4/2004 | Dao ........................... 422/62 |
| 2004/0084614 A1 | 5/2004 | Honjo |
| 2004/0255644 A1* | 12/2004 | Carlson et al. ............ 73/28.04 |
| 2005/0135973 A1* | 6/2005 | Quine et al. ................ 422/101 |
| 2005/0136540 A1* | 6/2005 | Quine et al. .................... 436/1 |
| 2005/0155410 A1 | 7/2005 | Manoosingh |
| 2005/0181520 A1* | 8/2005 | Ornath ....................... 436/181 |
| 2005/0214168 A1 | 9/2005 | Lin |
| 2006/0060006 A1* | 3/2006 | Ornath et al. ............ 73/864.33 |
| 2006/0213253 A1* | 9/2006 | Yoon ........................ 73/31.03 |
| 2007/0086925 A1* | 4/2007 | O'Donnell et al. .......... 422/100 |
| 2007/0228136 A1* | 10/2007 | Beckert et al. ................ 232/31 |

* cited by examiner

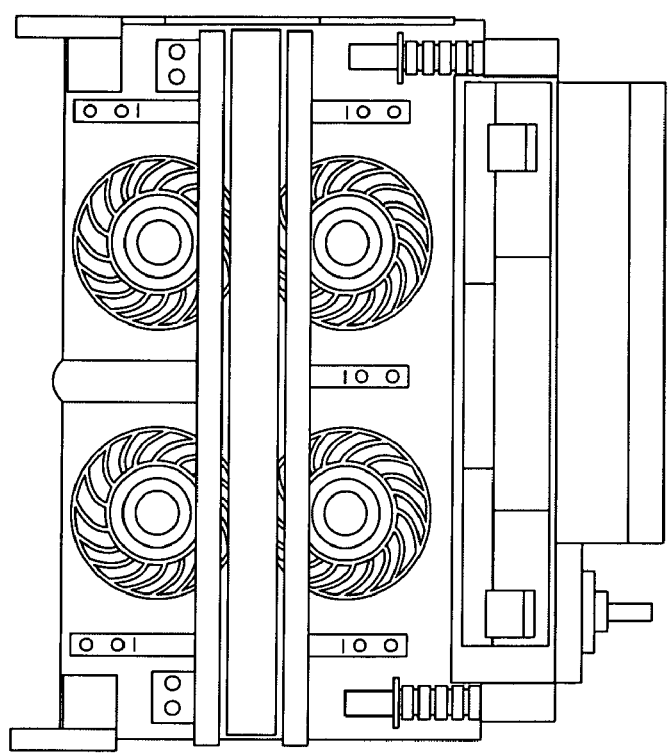
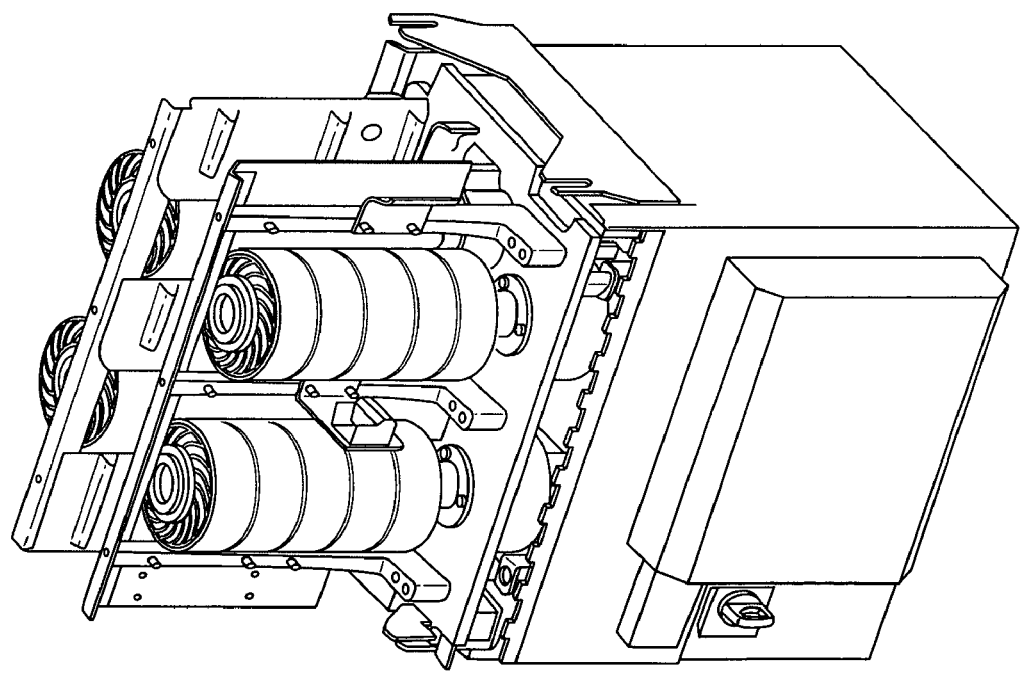
FIG. 1
*PRIOR ART*

```
                    ┌─────────────────────┐
                    │ SAMPLE COLLECTION   │
                    │       UNIT          │
                    │  ┌───────────┐      │
                    │  │  NOZZLE   │─ 122 │
                    │  └───────────┘      │      ┌─────────────────────┐
                    │                     │      │  SAMPLE ANALYSIS    │
                    │                     │      │       UNIT          │
                    │  ┌───────────┐      │      │  ┌───────────┐      │
  ┌─────────┐       │  │    AIR    │─ 124 │      │  │  IN-LINE  │─ 132 │
  │  MAIL   │───────│  │  SOURCE   │      │──────│  │ ANALYZER  │      │
  │ FEEDER  │       │  └───────────┘      │      │  └───────────┘      │
  └─────────┘       │                     │      │                     │
       └110         │  ┌───────────┐      │      │  ┌───────────┐      │
                    │  │  AEROSOL  │─ 126 │      │  │  ANALYZER │─ 134 │
                    │  │  CHAMBER  │      │      │  └───────────┘      │
                    │  └───────────┘      │      │                     │
                    │                     │      └─────────────────────┘
                    │  ┌──────────────┐   │              └130
                    │  │PARTICLE/AEROSOL│─128│
                    │  │  COLLECTOR   │   │
                    │  └──────────────┘   │
                    └─────────────────────┘
        100↗                 └120
```

FIG. 2

DEVICE AND METHOD FOR DETECTING HAZARDOUS MATERIAL IN MAIL

FIELD OF INVENTION

This invention relates generally to the detection of hazardous material and, in particular, to detection of hazardous material in letters and other mail packages.

BACKGROUND

There are many chemical, biological, and explosive threats that can be readily prepared and delivered in letter or flat mail pieces. Systems have been developed to extract and detect threat material contained within such mail pieces. These systems typically rely upon a series of opposing belts and rollers to pinch the mail piece and expel material contained within it. While the precise mechanism for particle expulsion has not been fully characterized, practical design experience and testing have demonstrated that a significant amount of threat material can be aerosolized and released from an envelope when passed through pinch rollers or belts. It is believed that as a letter passes through a set of pinch rollers, an air pocket forms that is eventually expelled through the end of the letter. The motion of the air in the letter acts to aerosolize threat material that is subsequently expelled from the envelope with the air.

FIG. 1 shows a prior art system in which a set of opposing pinch rollers are used to liberate particles. In this system, a piece of mail comes into contact with an initial set of opposing pinch wheels. The purpose of this first set of pinch wheels is to partially evacuate envelopes which have a relatively large amount of air trapped inside of them. This is necessary to prevent them from popping when traveling through the second set of pinch wheels. The gap between adjacent wheels allows a portion of the entrapped air within the flat envelope to shift into the pockets between adjacent wheels and gradually seep out of the envelope.

Once the envelopes have passed through the first set of pinch wheels they are immediately captured by the second set of pinch wheels. These wheels have a much greater force and do not have any gaps between adjacent wheels. Any remaining air within the envelopes is squeezed out the back of the envelope and into the air cavity between the two sets of wheels. If any hazardous materials are present in the envelope, a portion of them will be aerosolized and liberated during this process and will remain temporarily suspended in the air cavity between the two sets of pinch wheels. The aerosolized hazardous materials are then evacuated from the cavity between the two sets of wheels and passed along to analysis equipment. Detailed description of such belt-and-roller particle detection systems can be found in, for example, U.S. Pat. Nos. 6,941,794, 7,110,422 and 7,114,369.

While the belt-and-roller systems have been deployed and have proven to be effective, they generally cannot dislodge material contained on the exterior of an envelope. Moreover, the physical contact pinching mechanisms may damage the contents of a mail package. Therefore, there still exists a need for detection systems with improved performance.

SUMMARY OF THE INVENTION

One aspect of the present invention relates to a mail screening device for hazardous materials. The device comprises a sample collection unit having a nozzle that produces a flow of pressured air to dislodge residues of a hazardous material from a mail; and a detection unit that detects the hazardous material in an exhaust flow containing the residues of the hazardous material.

In one embodiment, the mail screening device further comprises a mail feeder that delivers mails to the sample collection unit.

In another embodiment, the sample collection unit comprises multiple nozzles arranged to produce air flows that form different angles with surfaces of the mail.

In a related embodiment, the nozzle produces an air flow in the form of an air jet or air knife.

In another embodiment, the nozzle produces a pulsed or continuous air flow.

In another embodiment, the nozzle produces an air flow of variable or constant pressure.

In yet another embodiment, the sample collection unit further comprises an air source.

Another aspect of the present invention relates to a method for detecting hazardous materials in the interior, or on the exterior, of a mail. The method comprises the steps of subjecting the mail to a stream of pressured air to dislodge residues of a hazardous material from the mail; collecting an exhaust flow of air from the mail; and detecting the hazardous material in the exhaust flow.

BRIEF DESCRIPTION OF DRAWINGS

FIG. 1 shows the side view and top view of a prior art detection system using a set of opposing pinch rollers to dislodge material contained inside an envelope.

FIG. 2 is a block diagram showing an embodiment of the mail screening device of the present invention.

FIG. 6A provides results for two letters processed by a prototype Flats Canceller Collection Module (FCCM), while FIG. 6B provides results from the air jet/knife test device.

DETAILED DESCRIPTION OF THE INVENTION

Figure 3A:
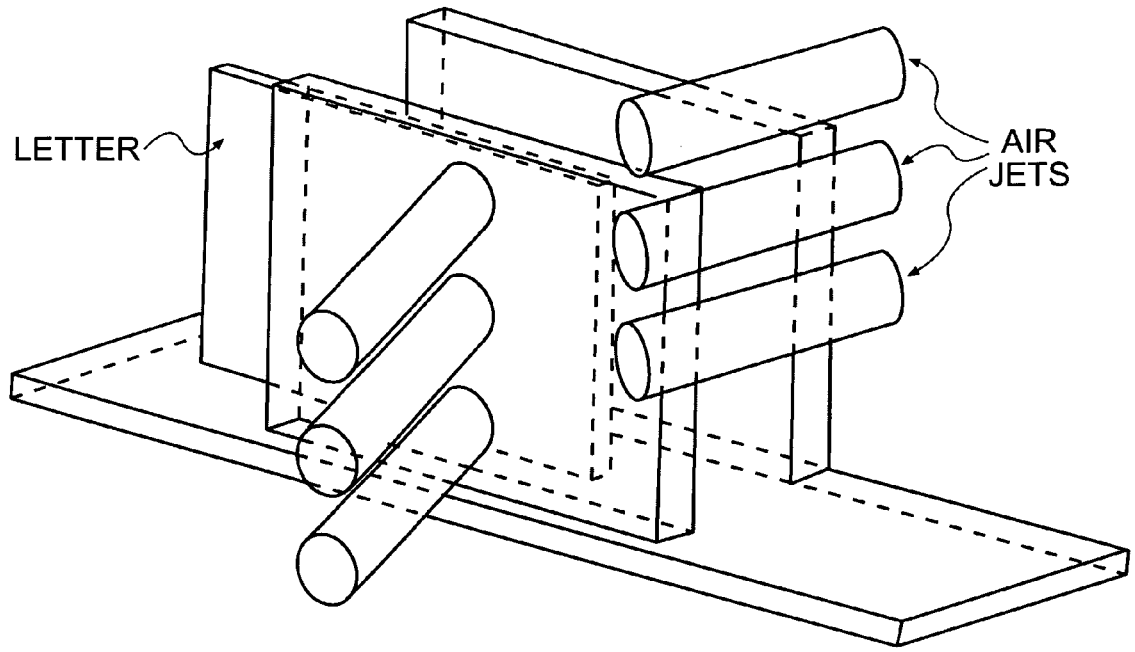
FIGS. 3A and 3B are diagrams depicting of opposing air jets (FIG. 3A) or air knives (FIG. 3B) interrogating and pinching an envelope as it moves past the bank of air knives/jets.

In describing preferred embodiments of the present invention, specific terminology is employed for the sake of clarity. However, the invention is not intended to be limited to the specific terminology so selected. It is to be understood that each specific element includes all technical equivalents which operate in a similar manner to accomplish a similar purpose.

One aspect of the present invention relates to a device for detecting hazardous material in letters or other mail packages. The device aerosolizes and extracts hazardous materials or residues thereof from the interior or the exterior of a mail package. The aerosolized mixture is then delivered to a detection system for subsequent analysis of the hazardous material.

Examples of the hazardous materials include, but are not limited to, chemical warfare agents (CWA), biological warfare agents (BWA), explosives, non-traditional agents (NTA) and dusty agents (DA), as well as residues of these agents, the decomposed substances from these agents, or chemicals that can be used to identify these agents.

Examples of CWA includes, but are not limited to, nerve agents such as Tabun, Sarin, and Soman; vesicants such as mustard and Lewisite; and cyanides.

Examples of biological warfare agents (BWA) include, but are not limited to, bacteria and viruses such as *Bacillus anthracis, Yersinia pestis, Vibrio cholerae, Francisella tularensis, Coxiella burnetii, Clostridium botulinum*, avian influenza virus, smallpox virus, Filoviruses, and hantaviruses, and biotoxins such as Staphylococcal enterotoxin B (SEB), racin, botulinum toxins, and the trichothecene mycotoxins.

Examples of explosives include, but are not limited to, nitroglycerin-based powders, ammonium nitrate/fuel oil mixtures (ANFO), Trinitrotoluene (TNT), Pentaerythritoltetranitrate (PETN), Cyclotrimethylenetrinitramine (RDX), and Cyclotetramethylene-tetranitramine (HMX).

Non-traditional agents (NTAs) and dusty agents (DAs) are CWAs or BWAs dispersed as either a liquid or particulate aerosol.

For the purposes of this disclosure, a residue is considered to be a small amount of a substance, or a material associated with that substance. A residue may not directly be the substance whose detection is desired, but may be a substance indicative of the presence of the first substance. For instance, a residue of a hazardous material may be a degradation product of a hazardous material, a chemical binder used to particulate a gaseous CWA, or a substrate on which a BWA is placed.

FIG. 2 shows an embodiment of the hazardous material detection device of the present invention. The hazardous material detection device 100 comprises a mail feeder 110, a sample collection unit 120, and a sample analysis unit 130.

The mail feeder 110 comprises means that are capable of bringing mails to the sample collection unit 120 in desired positions and speed. As used herein, the term "mails" and "mail packages" include letters, envelops, flats (large but thin envelopes) and thicks (packages or boxes). The mail feeder 110 can be part of, or connected to, a mail collecting and sorting system commonly used in the United States Postal Service facilities, such as those described in U.S. Pat. Nos. 6,941,794, 7,110,422 and 7,114,369, which are hereby incorporated by reference in their entirety.

In one embodiment, the mail feeder 110 comprises conveyer belt that brings mails into the sample collection unit 120. The conveyer belt may contain rollers or similar devices to hold the mails in positions to facilitate interrogation in the sample collection unit 120. In another embodiment, letters and flats are separated from thicks on the conveyer belt before entering the sample collection unit 120.

To minimize exposure to employees and reduce cost, a contaminated letter is preferably identified early in the mail processing cycle. The further the contaminated mail is allowed to travel before it is detected, the more it spreads throughout the facility and the more people who are potentially exposed to it. In a mail collection facility, mail typically enters the facility in hampers which are large bags or other containers of mail which have been created at the facility or have been transferred to the facility. The hampers are then dumped into a Dull Pass Rough Cull System (DPRCS) which separates the mails into thicks, flats and letters. The separated mails are then sent to sorting machines by different conveyers. As the mail spreads out, not only do the number of sensing systems that would be needed to detect a contaminant increase dramatically, but should a contaminated mail piece be found, the number of mail processing systems that must be decontaminated also rises dramatically as does the number of employees exposed to the potentially lethal agent. Further, it can become harder and harder to localize the source of the contaminant as the source may have contaminated many other mail pieces that it was in contact with. It is therefore desirable to detect the contamination at the earliest possible opportunity. In one embodiment, the mail screening device of the present invention is installed at the DPRCS or a comparable level of the mail sorting system.

The sample collection unit 120 utilizes air jet/knife technology to interrogate the mail and dislodge hazardous materials or residues of hazardous materials contained in the interior and on the exterior of a mail package. As used herein, the term "air" includes the ambient air in the atmosphere and any other gaseous materials, such as nitrogen and carbon dioxide, that can be used to generate a pressured flow to dislodge hazardous materials from a mail. In one embodiment, the sample collection unit 120 comprises an air nozzle 122, a pressured air source 124, an aerosol chamber 126, and a sample collector 128.

Specifically, the air nozzle 122 is arranged in configurations that mimic the pinching mechanism of physical pinching rollers or belts. More than one air nozzle 122 may be used. In a preferred embodiment, a letter will be completely pinched shut from the top to the bottom of the envelope by pressured air. Depending on the shape of the air exit in the air nozzle 122, an air jet (circular or polygon shaped air exit) or an air knife (slit shaped air exit) is produced. Air jet and air knife technologies are well known to one skilled in that art. In one embodiment, the air nozzle 122 is a commercial off-the-shelf product. Air nozzles of various shapes and sizes are available at, for example, Spraying Systems Co. in Wheaton, Ill. and Silvent in Portage, Ind.

Figure 3B:
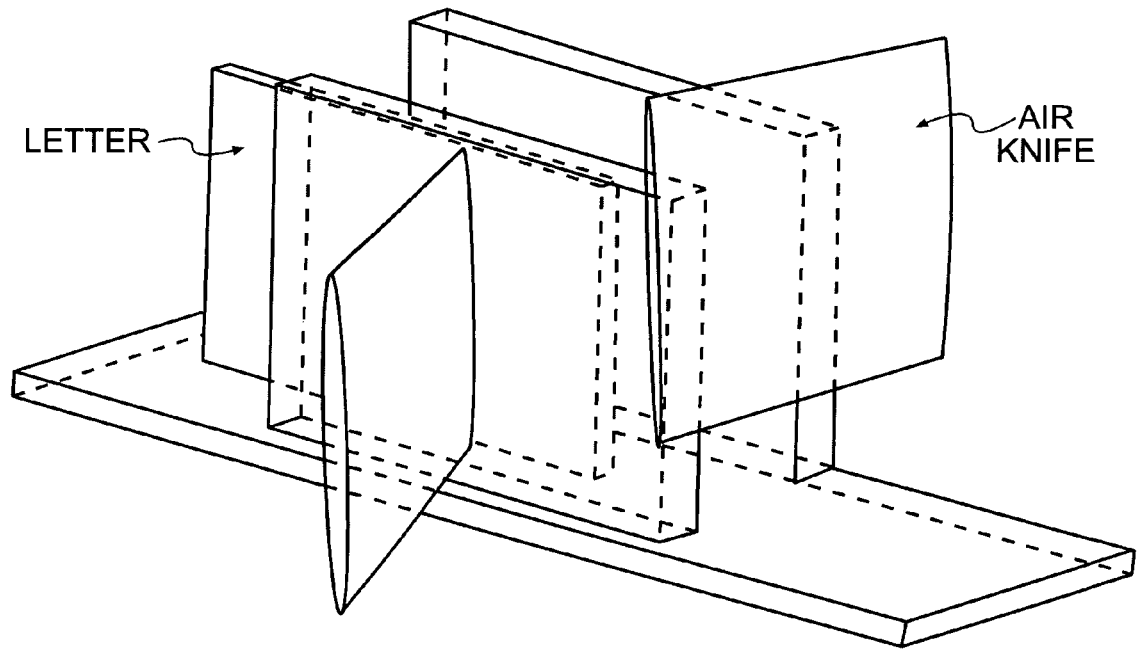

FIGS. 3A and 3B show representative configurations of air jets (FIG. 3A) and air knives (FIG. 3B), respectively. One skilled in the art would understand that the orientation of the air jet or air knife to the mail in FIGS. 3A and 3B is for demonstration only, the optimal design may differ and many other configurations may be used. For example, instead of using pairs of air jets or air knives, the mail package may be placed between one air jet (or one air knife) and a solid surface. Typically, the air nozzle 122 is connected to a filtered and pressure-regulated air source 124, and is placed within a predetermined distance from the conveyor belt that delivers the mail. For boxes or mail packages with irregular shapes, multiple air jets or air knives may be used to create air impact from multiple angles. When a mail package approaches the air nozzle 122, a pulse of air is produced to pinch the mail package and squeeze out the air within the mail package from the back of the mail package. The hazardous materials present in the package or on the exterior of the package will be aerosolized and liberated during this process and will remain temporarily suspended in the exhaust flow, which will be collected for analysis in the sample detection unit 130.

The air source 124 can be a compressed air system or a blower-driven air system. Both systems are commercially available and well-known to one skilled in the art.

The number and positions of the air nozzles 122, the pressure of the air flow (in the form of air jet or air knife), and the speed of the conveyor belt, may be optimized for each particular configuration. In one embodiment, the air nozzle 122 produces a pulsed air flow and the timing of the air pulse is controlled by an electronic solenoid-activated valve. In another embodiment, the air nozzle 122 produces a continuous air flow with constant or variable pressure. In one embodiment, air source 124 is a compressed air system with a pressure up to 150 psi, preferably in the range of 10-150 psi. In another embodiment, the air source is a blower-driven air system with an air flow rate up to 1500 liter per minute (LPM), preferably in the range of 100-1500 LPM.

The hazardous materials suspended in the exhaust flow are analyzed by the sample analysis unit 130. In one embodiment, the exhaust air flow from the mail enters the aerosol chamber 126 and the hazardous materials are detected real time using an in-line analyzer 132. In another embodiment, the exhaust air flow from the mail enters the aerosol chamber 126 that connected to the sample collector 128. The hazardous materials are collected by the sample collector 128 and then subject to analysis by analyzer 134.

The aerosol chamber 126 is preferably held at negative pressure by drawing air into intake plenums so that any aerosolized residue from the mail is left behind in an internal area of the chamber as the mail passing through the sample collection unit 120. The negative pressure is created and maintained by evacuating the air surrounding the air nozzle 122 at a rate that is at least 20% larger than the flow rate coming out of the air nozzle 122. For example, if the air nozzle 122's blow out rate is 1000 LPM, the air evacuating rate around the nozzle should be at least 1200 LPM. Examples of aerosol chambers can be found in U.S. Pat. Nos. 6,941,794, 7,110,422 and 7,114,369, which are hereby incorporated by reference in their entirety.

The sample collector 128 can be any type of particle/aerosol collector capable of collecting the particles or aerosols of interest. Examples of the particle/aerosol collector 128 include, but are not limited to, electrostatic collectors, virtual impactors, regular plate impactors, and filter-based particle collectors.

The hazardous materials can be detected with a wide variety of detection methods as are known to those of ordinary skill in the art. Typically, a detection method is chosen based on the hazardous materials of interest. For example, CWAs and explosives may be detected with Raman spectroscopy, infrared spectroscopy (IRS), mass spectrometry (MS), gas chromatography (GC), Fourier transform infrared spectrometry (FTIRS), ion mobility spectrometry (IMS), photoacoustic infrared spectroscopy (PAIRS), and in-flame photometry (IFP).

BWAs may be detected with fluorescence aerosol particle sizing (FAPS), flow cytometry, and flame photometry. FAPS is a combination of Aerodynamic Particle Sizing technology and fluorescence technology (UV-LIF) in a single system. Flow cytometry measures particle sizes and counts particles in liquid suspensions through use of laser scattering. Typically, the sample is also treated with fluorescent dye that reacts with biological material. Flame photometry, also known as flame atomic emission spectrometry, for biological detection is based on the phosphorous content of biological material that is visible to flame photometry.

Examples of the sample analyzer 132 or 134 also include the aerosol particle analyzer described in the U.S. Patent Application Publication No. 2005/0214168 (detection with electrostatic forces), the chemical agent detection apparatus described in the U.S. Patent Application Publication No. 2004/0084614 (detection with counter-flow atmospheric pressure ionization (APCI) and mass spectrometry (MS)), and the chemical agent detector described in the U.S. Patent Application Publication No. 2005/0155410 (detection with surface acoustic wave (SAW)). These patent applications are hereby incorporated by reference in their entirety.

Comparing to mail screening systems using physical pinching mechanisms, the air jets/knives design of the present invention provides similar or better performance at lower cost and complexity. Furthermore, the air jets/knives further enhance system performance by dislodging hazardous materials contained on the exterior of a mal package, which is not detectable by the current physical pinching mechanisms. This could provide a substantial boost in system performance as residual material from envelope preparation is likely to remain on the exterior surfaces, even after wiping the envelope clean. In addition, the air-based technology will potentially reduce damage to envelopes and their contents.

Figure 4:
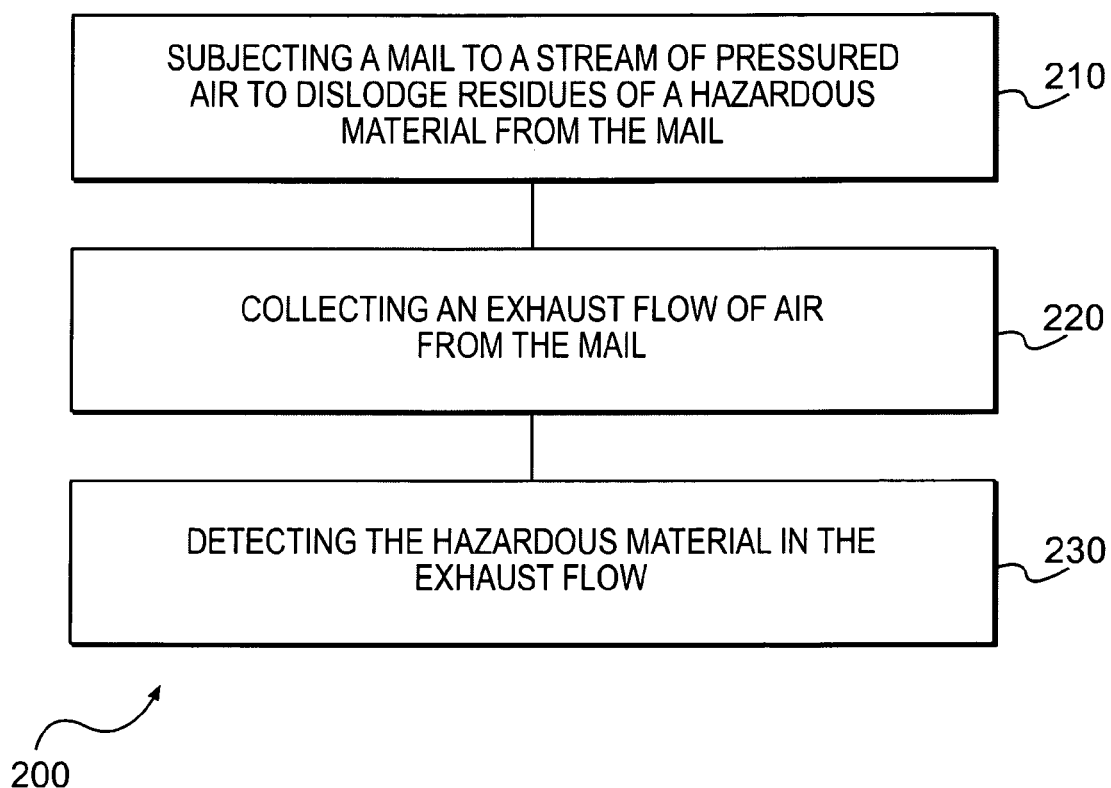
FIG. 4 is a flow diagram showing the mail screening method of the present invention.

Another aspect of the present invention relates to a method for screening mails for hazardous materials. As shown in FIG. 4, the method 200 include the steps of: subjecting (210) a mail to a stream of pressured air to dislodge residues of a hazardous material from the mail, collecting (220) an exhaust flow of air from the mail, and detecting (230) the hazardous material in the exhaust flow. In one embodiment, the hazardous material is detected in real time. In another embodiment, the mail is subjected to multiple streams of pressured air to dislodge residues of the hazardous material from the mail.

EXAMPLES

Example 1

Figure 5:
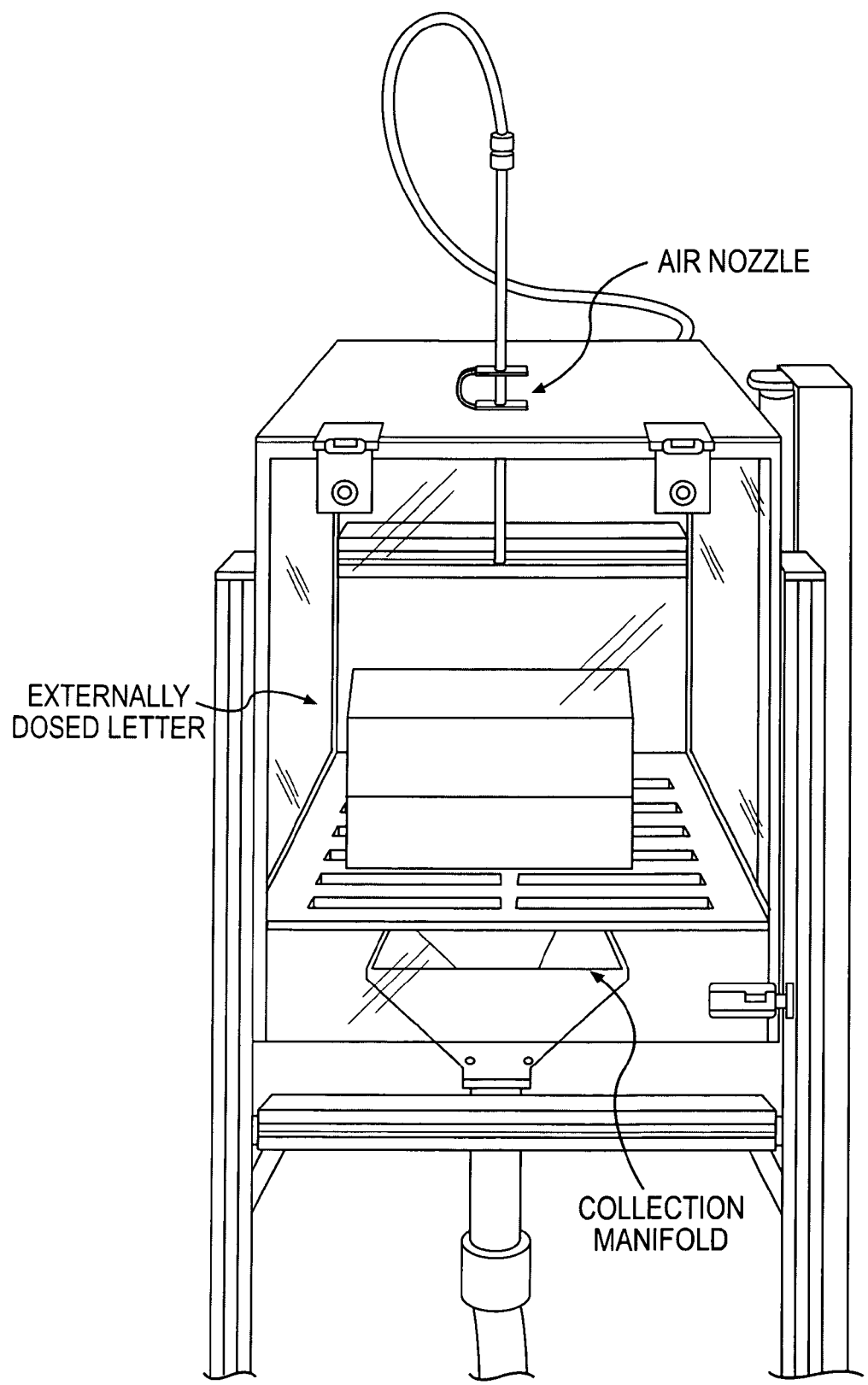
FIG. 5 is a picture of a prototype mail screening test device.

Preliminary Trials on the Efficacy of Using Air Jets/Knives to Extricate Particles from the Surface or Interior of Letter Mail A test bed comprising a pair of air jets/knives, a transfer belt capable of passing an envelope through the air jets/knives, a collection manifold positioned under the air jet/knives, and a detection system (FIG. 5).

Trials were conducted by first dosing tri-folded piece of paper with a small, weighed quantity of Visolite particulates (1-10 μm fluorescent particles). The paper was then placed inside a standard envelope and sealed. The air jet nozzles/knives were then positioned a measured distance from the envelope surface and connected to a filtered and pressure-regulated compressed air source. An electronic solenoid-activated valve was used to control the timing of the pulse of air. The internally dosed letter was attached to a non-invasive enclosure and drawn past the air jets/knives using a linear actuator; for comparison, similarly dosed letters were processed by a prototype Flats Canceller Collection Module (FCCM) that used a traditional belt-and-roller pinching mechanism. The particulates in the exhaust flow were detected using an in-line particle counter (particle size distribution).

Even with a non-optimized test stand, preliminary trials showed that the performance of air jets/knives was comparable to or better than the performance of physical pinch rollers. Compared to the FCCM, the air jet/knife test stand routinely extracts a similar or greater total number of particles from each letter (see Table 1).

Figure 6A:
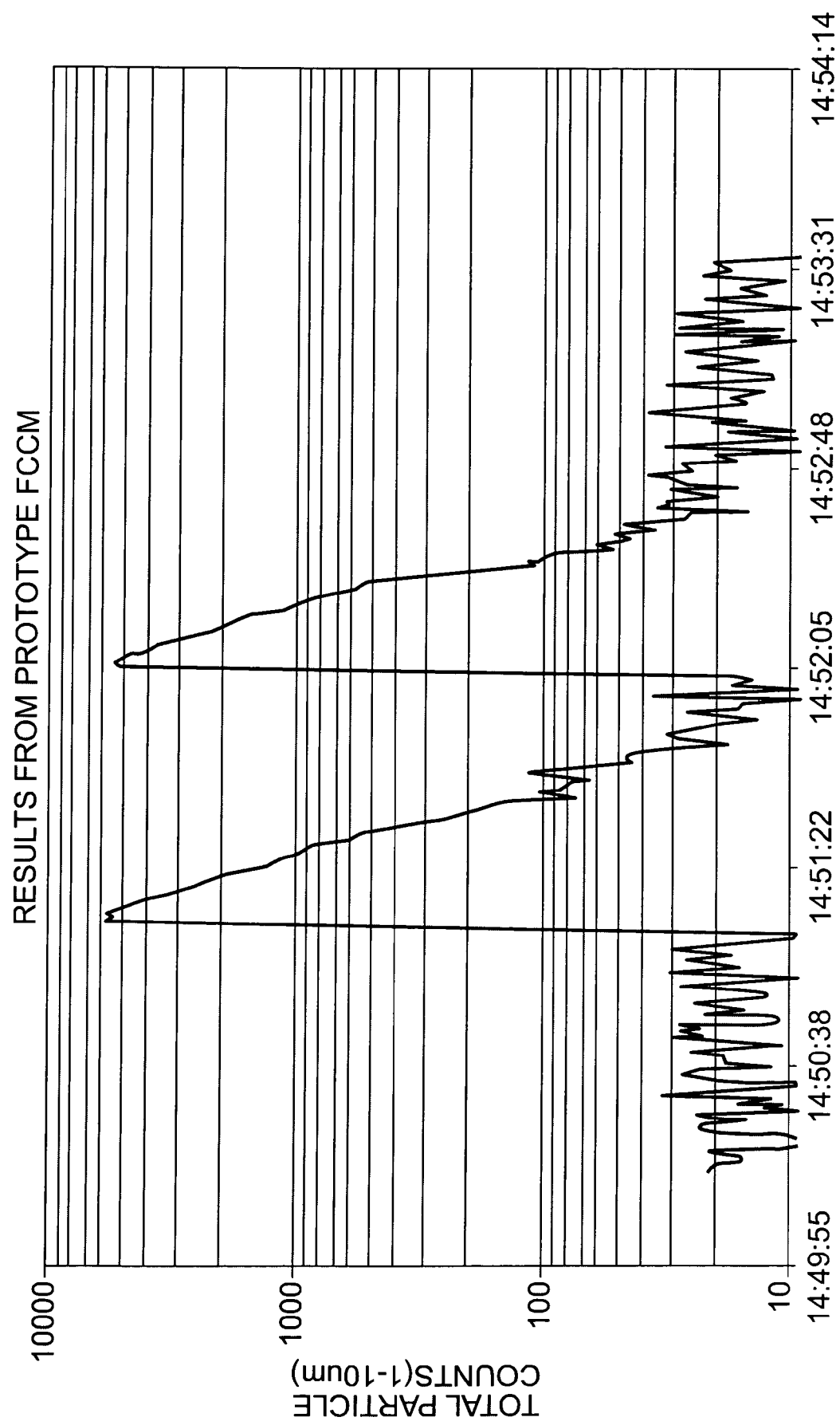
FIGS. 6A and 6B are diagrams showing the number of particles released and collected from internally dosed letters.
Figure 6B:
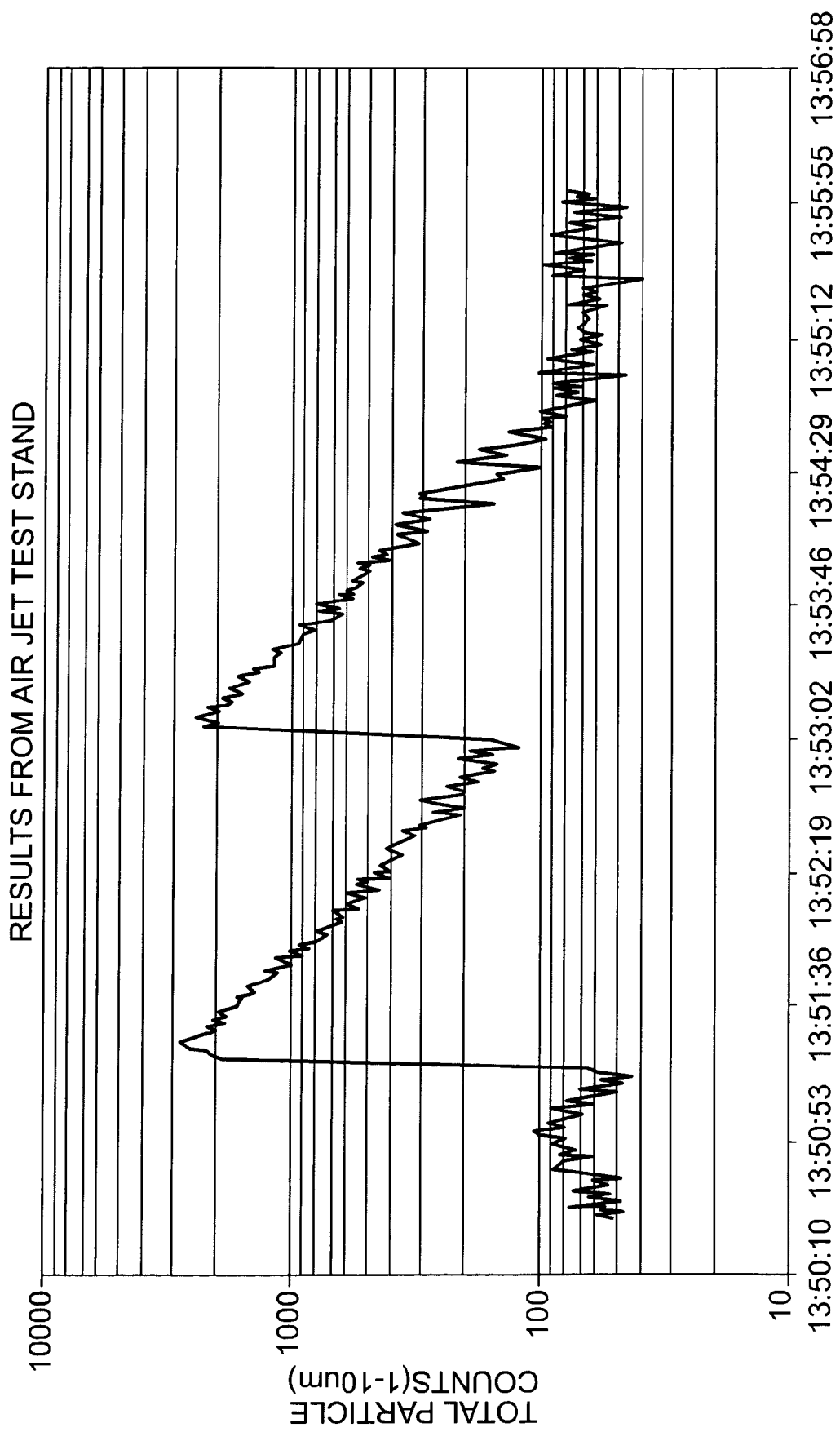

FIGS. 6A and 6B show the number of particles released and collected from two internally dosed letters by the prototype FCCM (FIG. 6A) and the air jets/knives test stand (FIG. 6B). Each pulse in the diagrams represents a letter that is pinched by either the rollers or the air jets/knives. The shape of the curves differ because the volume of the chambers surrounding the pinchers differ (i.e. the test stand has a larger volume, thereby it takes longer to evacuate).

TABLE 1

Total number of particles extracted (excluding background noise) from each letter processed during the trials shown in FIGS. 6A and 6B

| Total Number of Particles Extracted From the: | Pinching Rollers (FIG. 6a) | Air Jet/Knife (FIG. 6b) |
|---|---|---|
| First Letter | 57,404 | 82,935 |
| Second Letter | 49,053 | 69,719 |

Figure 7:
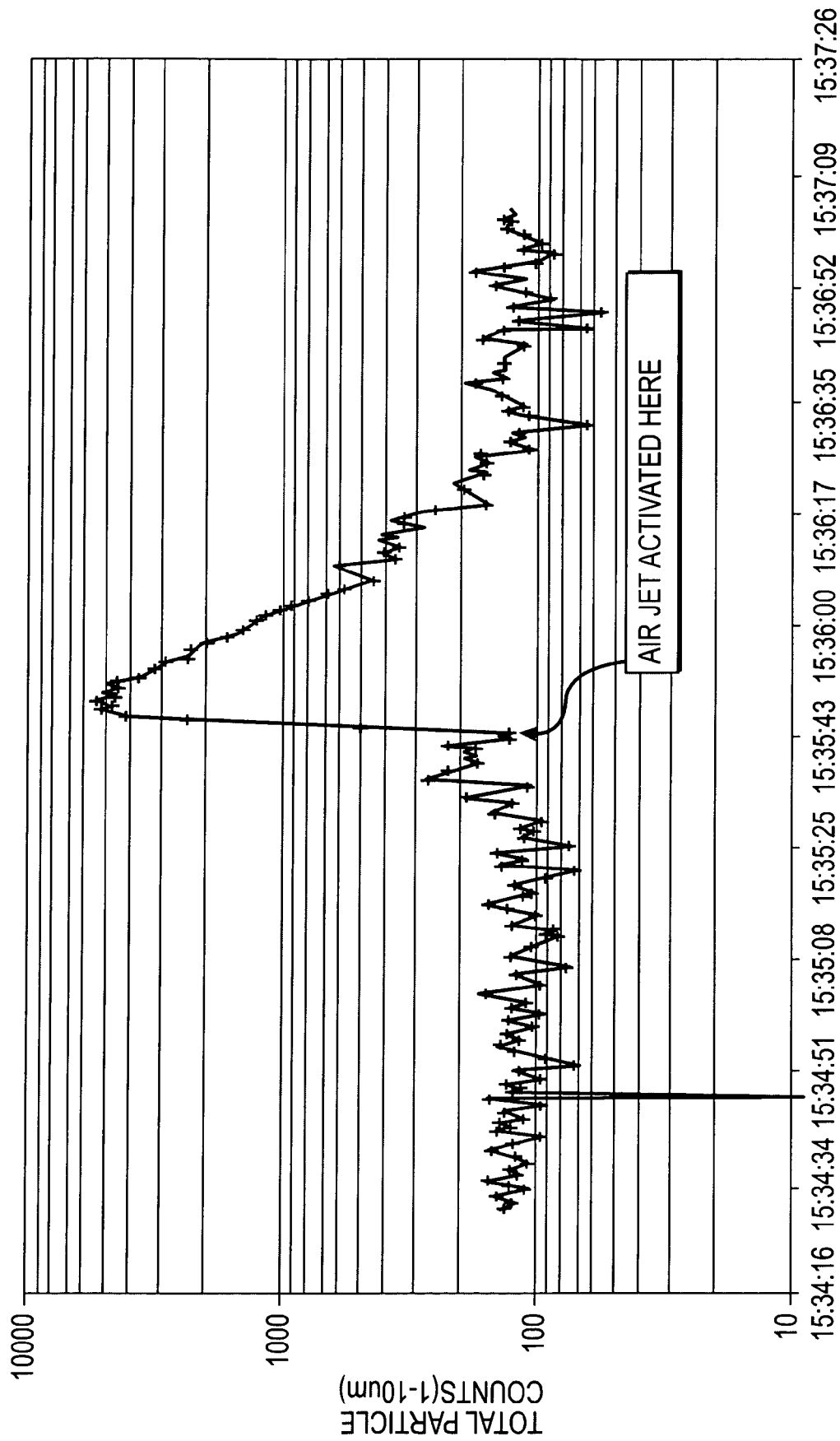
FIG. 7 is a diagram showing the number of particles released and collected from a thumb print on a mail.

In another trial, the air jets/knives test stand was used to dislodge unintentional trace material left on a package by a thumb print. The trial intended to mimic a plausible threat scenario by smearing 1 mg of Visolite onto a package surface with a bare thumb, then wiping the box with a towel to remove excess particles. The 'contaminated' box was placed into the test bed and pulsed with a 70 psi air jet positioned 6 cm from the surface. The results, shown in FIG. 7, clearly showed the increase in target particle levels when the air jet was applied. Similar results are anticipated when a letter exterior is dosed.

Figure 8:
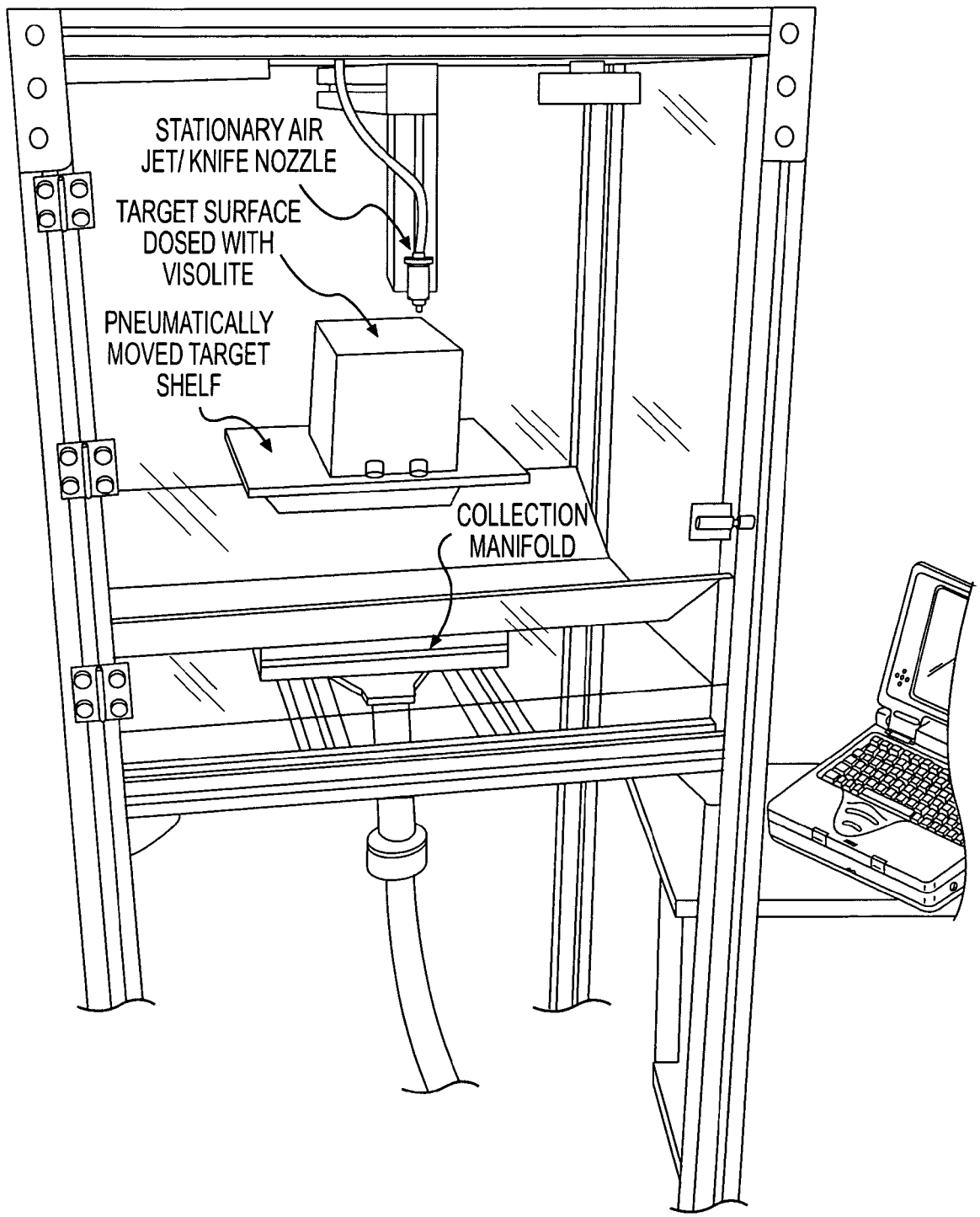
FIG. 8 is a picture of a refined prototype mail screening test device.

In yet another trial, a test stand incorporating critical concept design elements was created (FIG. 8). The test stand contains an air jet/knife, a shelf for moving the target past stationary air knives/jets, a collection manifold positioned under the package, a detection system, and a collection system. The test stand was automated such that depressing a trigger button would activate a valve to release compressed air into the air jet/knife and then move the target past the bank of stationary air jets/knives. A downstream particle counter measured and logged the particle release event.

Repeatable, real world trials were conducted through automating the test stand. As the trials were conducted to determine if air jets/knives could be used to extricate particles from the exterior and interior of a letter, relatively optimal test conditions were used. This included positioning the jet a small distance from the letter surface (6 inches) at a moderate pressure (70 psi). A typical test was conducted by first preparing the letter by weighing 10 mg of Visolite particulates and depositing the particles in a tri-folded piece of paper. The paper was then placed in a standard envelope and sealed. An undosed envelope was used to determine the background amount of dislodged particles.

After the collection system's blower motor reached steady airflow, and the aerosol particle counter was started, each trial would automatically (and hence repeatably) commence when a start button was depressed. After the button was depressed, an electronic solenoid-activated valve was opened to send compressed air to the air jet/knife. The pneumatic pump then moved the target past the stationary air jet/knife. The jet was then turned off. Dislodged particles in the exhaust flow were detected and collected using an in-line particle counter (to obtain the particle size distribution) and an impaction-based collector. Each trial was performed at the least in triplicate.

Figure 9:
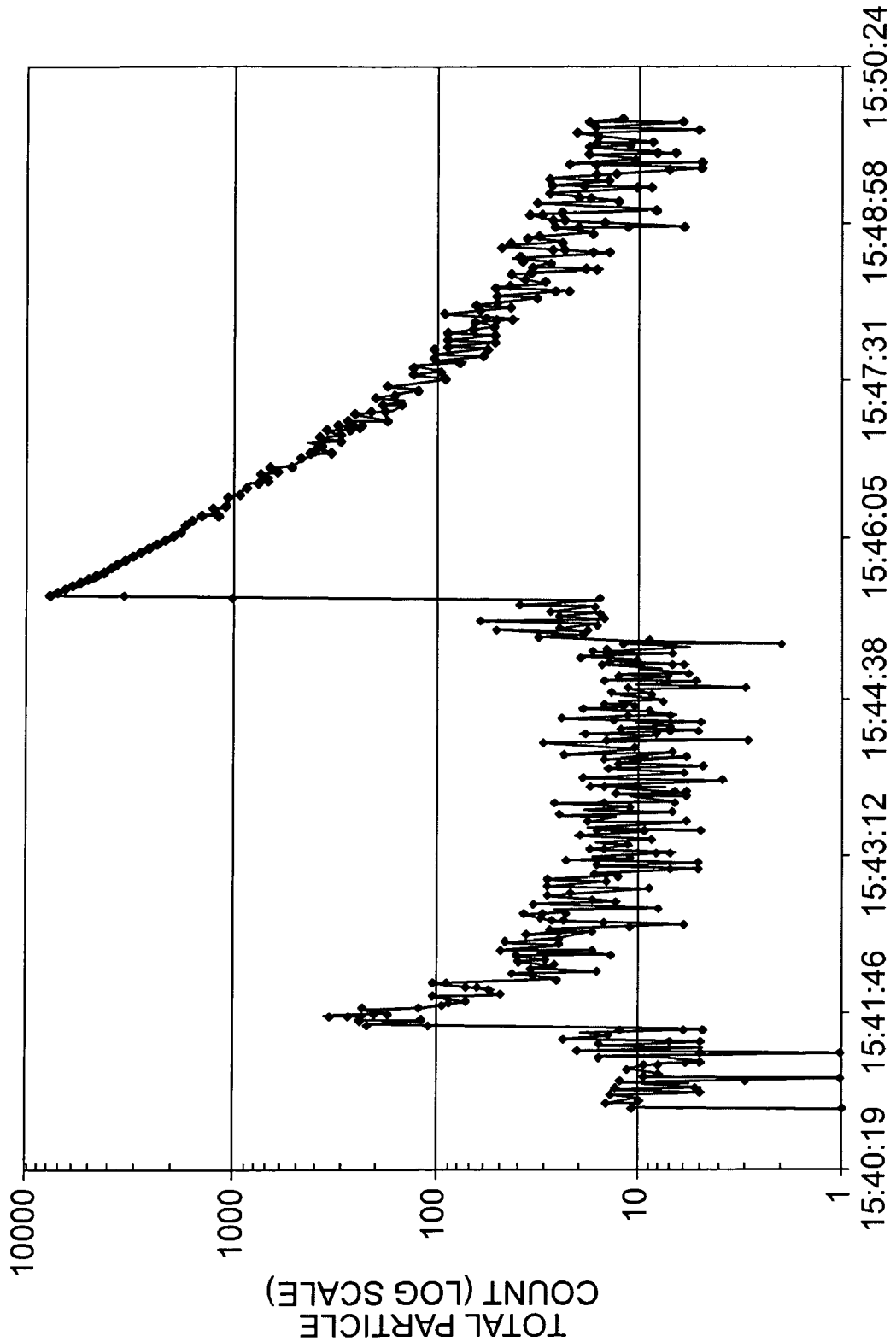
FIG. 9 is a diagram showing the number of particles released and collected from a blank envelope (left pulse) and particle loaded envelope (right pulse).

The result from a test run is shown in FIG. 9. The test run was conducted by passing both blank envelopes (with no Visolight) and loaded envelopes (with Visolight within a tri-folded piece of paper) through a bank of air jet. As shown in FIG. 9, there is a discernable amount of Visolight particles released from the loaded envelopes as compared to the background noise from the blank envelopes. This study involved 3 blank envelope replicates and 6 loaded envelopes. It was found that the blank envelopes released an average of 10,000 particles, while roughly 120,000 particles were released from the loaded envelopes. This result validates that the concept of using banks of air jets/knives can remove particles from the interior of letters.

For comparison, identically prepared blank and loaded envelopes were run through an FCCM that used physical pinch rollers to release particles from the interior of envelopes. It was found that blank envelopes were not discernable from background noise, while roughly 40,000-50,000 particles were released from loaded envelopes. Given that the air jets/knives released ~120,000 particles, this study demonstrates that banks of air knives/jets can be effectively employed in the screening of mail.

The embodiments illustrated and discussed in this specification are intended only to teach those skilled in the art the best way known to the inventors to make and use the invention. Nothing in this specification should be considered as limiting the scope of the present invention. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

What is claimed is:

1. A mail screening device for hazardous materials, comprising:
    a sample collection unit comprising:
    at least one nozzle arranged in a configuration that mimics the pinching mechanism of physical pinching rollers or belts, wherein said nozzle produces a flow of pressured air capable of dislodging residues of a hazardous material contained in the interior and on the exterior of a mail package; and
    a detection unit that detects said hazardous material in an exhaust flow containing said residues of said hazardous material.

2. The mail screening device of claim 1, wherein said a sample collection unit comprises multiple nozzles arranged to produce air flows that form different angles with surfaces of said mail.

3. The mail screening device of claim 1, wherein said nozzle produces an air flow in the shape of an air knife.

4. The mail screening device of claim 1, wherein said nozzle produces a continuous air flow.

5. The mail screening device of claim 1, wherein said nozzle produces an air flow of variable pressure.

6. The mail screening device of claim 1, wherein said nozzle produces an air flow of constant pressure.

7. The mail screening device of claim 1, wherein said nozzle produces an air flow in the shape of an air jet.

8. The mail screening device of claim 1, wherein said detection unit comprises an in-line analyzer that detects said hazardous material in said exhaust flow in real time.

9. The mail screening device of claim 1, wherein said sample collection unit comprises a particle/aerosol collector that traps said residues of the hazardous material in said exhaust flow.

10. The mail screening device of claim 1, wherein said hazardous material is selected from the group consisting of chemical warfare agents, biological warfare agents, explosives, non-traditional agents or dusty agents.

11. The mail screening device of claim 1, wherein said hazardous material is a bacteria spore.

12. The mail screening device of claim 1, further comprising a mail feeder that delivers mails to said sample collection unit.

13. The mail screening device of claim 12, wherein said mail feeder is a conveyer belt.

14. The mail screening device of claim 1, wherein said nozzle produces a pulsed air flow.

15. The mail screening device of claim 14, further comprising an electronic solenoid-activated valve that controls timing of said pulsed air flow.

16. The mail screening device of claim 1, further comprising an air source.

17. The mail screening device of claim 16, wherein said air source is a compressed air system or a blower-driven air system.

18. A method for detecting hazardous materials in the interior, or on the exterior of a mail, comprising:

subjecting said mail to a stream of pressured air that mimics the pinching mechanism of physical pinching rollers or belts to dislodge residues of a hazardous material from the interior and exterior of said mail;

collecting an exhaust flow of air from said mail; and detecting said hazardous material in said exhaust flow.

19. The method of claim 18, wherein said hazardous material is detected in real time.

20. The method of claim 18, wherein said mail is subjected to multiple streams of pressured air to dislodge residues of said hazardous material from said mail.

* * * * *